United States Patent [19]

Kondo et al.

[11] Patent Number: 4,526,987
[45] Date of Patent: Jul. 2, 1985

[54] ALKYL 6,6-DIMETHYL-2-OXO-3-OXABICYCLO[3.1.0]HEXANE-1-CARBOXYLATES

[75] Inventors: Kiyoshi Kondo, Yamato; Toshiyuki Takashima, Ebina; Daiei Tunemoto, Sagamihara, all of Japan

[73] Assignee: FMC Corporation, Philadelphia, Pa.

[21] Appl. No.: 736

[22] Filed: Jan. 3, 1979

Related U.S. Application Data

[63] Continuation-in-part of Ser. No. 875,649, Feb. 6, 1978, abandoned.

[51] Int. Cl.³ .......................................... C07D 307/77
[52] U.S. Cl. .................................. 549/305; 549/302; 560/174; 560/178; 560/168; 560/169; 562/506
[58] Field of Search ................. 260/343.3 R; 549/302, 549/305

[56] References Cited

U.S. PATENT DOCUMENTS

| 2,167,168 | 7/1939 | Boese . | |
|---|---|---|---|
| 3,723,469 | 3/1973 | Martel | 260/343.3 R |
| 3,836,568 | 9/1974 | Higo et al. . | |
| 3,868,401 | 2/1975 | Aratani et al. | 560/124 |
| 3,989,654 | 11/1976 | Honda et al. . | |
| 4,000,180 | 12/1976 | Punja | 560/124 |
| 4,014,918 | 3/1977 | Martel | 260/343.3 R |
| 4,024,163 | 5/1977 | Elliott et al. . | |
| 4,029,690 | 6/1977 | Aratani et al. | 560/124 |
| 4,132,717 | 1/1979 | Roman | 260/343.21 |
| 4,166,063 | 8/1979 | Martel | 260/343.3 R |

FOREIGN PATENT DOCUMENTS 856002 10/1977 Belgium .
51-122041 10/1976 Japan .

OTHER PUBLICATIONS

Aratani et al., Tetrahedron Letters 21, 1707, 1975 and 30, 2599 (1977).
Coates et al., J. Am. Chem. Soc. 93, 1785, 1971.
Danishefsky et al., J. Am. Chem. Soc. 99, 4785, 1977.
Franck-Neumann, Angew. Chem. Int. Ed. Engl. 7, 65 (1968).
Hirai et al., Agr. Bio. Chem. 40, 169, 1976.
Nozaki, et al., Tetrahedron, 24, 3655, 1968.
Ando, et al., J. C. S. Comm. 822, 1972.
Ando et al., J. O. Chem. 37, p. 3596, 1972.
Blomquist et al., J. Am. Chem. Soc. 70, 36 (1948).
Boese Ind. Eng. Chem. 32, 16 (1940).
Cahn et al., Angew. Chem. Intern. Ed. Engl. 5, 385 (1966).
Cannic et al., Bull Soc. Chim. France 4913, 1968.
Clark et al., Tetrahedron Letters 529, 1975.
Corey et al., J. Am. Chem. Soc. 94, 4014 (1972).
Elliott et al., J. Agric. Food Chem. 24, 270 (1976).
House et al., J. Org. Chem., 33, 53 (1968).
Kaneda et al., Bull Chem. Soc. Japan 40, 228 (1967).
Kirmse et al., Chem. Ber. 98, 4027 (1965).
Kondo et al., Tetrahedron Letters 4489 (1976).
Maior et al., Chem. Ber. 101, 1354 (1968).
March, Advanced Org. Chem. McGraw-Hill Book Co., pp. 771-772.
McMurry et al., Tetrahedron Letters 2575, 1971.
Migita et al., Chem. Abst. 78, 123954g (1973).
Organic Syn. Coll. vol. V, pp. 155-157, 1973, pp. 179-183, pp. 258-263.
Regitz, Angew. Chem. Int. Ed. Engl. 6, 733 (1967).
Regitz Synthesis 351 (1972).
Roush et al., Tetrahedron Letters 1391 (1974).
Shroff et al., J. Org. Chem. 36, 3356 (1971).
Stork et al., J. Am. Chem. Soc. 83, 4678 (1961).
Ziegler et al., Tetrahedron Letters 2035, 1974.
Regitz, Chem. Ber. 99, 3128, 1966.
Martel Chem. Abst. 121078b, vol. 72, 1970.
Martel Chem. Abst. 100139g, vol. 72, 1970.
Servin et al., Tetrahedron Letters, No. 43, pp. 3915-3918, 1976.

Primary Examiner—Jane T. Fan
Attorney, Agent, or Firm—R. L. Hansen; H. R. Ertelt

[57] ABSTRACT

Lactones of the formula

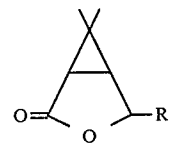

wherein R is hydrogen or a $CX_3$ group, and each X is a chlorine or bromine atom, are converted to the known cis-3-(2,2-dihalovinyl)-2,2-dimethylcyclopropanecarboxylic acids or lower alkyl esters, from which pyrethroid insecticides are obtained.

4 Claims, No Drawings

ALKYL 6,6-DIMETHYL-2-OXO-3-OXABICYCLO[3.1.0-]HEXANE-1-CARBOXYLATES

This is a continuation in part of application Ser. No. 875,649, filed Feb. 6, 1978, now abandoned.

This invention relates to novel intermediates for the production of cis-3-(2,2-dihalovinyl)-2,2-dimethylcyclopropanecarboxylates which are pyrethroid insecticides and to processes for making the intermediates.

Pyrethrins, naturally-occurring extracts of chrysanthemum flowers, have long been of interest as insecticides. Certain man-made variations of the natural pyrethrins are much more potent than the natural materials and exhibit other advantages. U.S. Pat. No. 4,024,163 discloses 3-(2,2-dihalovinyl)-2,2-dimethylcyclopropanecarboxylic acids, corresponding lower alkyl esters, and pyrethroid insecticides prepared from them. The acids and esters contain the following carboxylate radical, wherein X is chlorine or bromine.

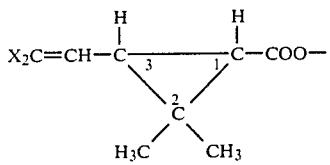

To produce pyrethroid insecticides, the acids or the lower alkyl esters may be esterified (or transesterified) with various alcohols, e.g., m-phenoxybenzyl alcohol, α-cyano-m-phenoxybenzyl alcohol, and other alcohols well known to those skilled in the art.

These acids and esters are known to exist as both cis and trans geometrical isomers; the carboxy and dihalovinyl groups at C-1 and C-3 may be either cis or trans with respect to each other. There are substantial differences in insecticidal activity between pyrethroid esters made from the cis and trans isomers of a given dihalovinylcyclopropanecarboxylic acid. In general, as between the cis and trans isomers of a given synthetic pyrethroid ester, the cis isomer is more active than the trans; the relative activities are reversed in the natural esters.

C-1 and C-3 are assymetric, and the pyrethroid esters may be optically active, their activity depending upon the stereoconfigurations at C-1 and C-3. In general, the (1R,3R) isomers are the most active. Optical isomers are named herein according to the "sequence rule" [see Cahn, et al., Angew. Chem., Intern. Ed. Engl., 5, 385 (1966)].

Because of the greater insecticidal activity of the cis esters, processes for producing cis-3-(2,2-dihalovinyl)-2,2-dimethylcyclopropanecarboxylates, essentially free of the trans isomers, are actively being sought.

Therefore, an object of this invention is to provide improved methods for producing both racemic and optically active cis-3-(2,2-dihalovinyl)-2,2-dimethylcyclopropanecarboxylic acids and lower alkyl esters essentially free of the trans isomers. Another object is the provision of novel intermediates for their production. Other objects will be apparent to those skilled in the art to which this invention pertains. The cis-3-(2,2-dihalovinyl)-2,2-dimethylcyclopropanecarboxylic acids and lower alkyl esters produced according to this invention may be esterified and converted into pyrethroid insecticides, with essentially no racemization or isomerization, according to methods disclosed in the prior art and well known to those skilled in the art. For example, the acid may be treated with thionyl chloride to produce the acid chloride, followed by reaction with an appropriate alcohol to produce an insecticidal ester, and the lower alkyl ester may be transesterified with an appropriate alcohol, both as disclosed in U.S. Pat. No. 4,024,163 or in Elliott, et al., J. Agric. Food Chem., 24, 270 (1976), which disclosures are incorporated herein by reference.

This invention includes both process and composition embodiments. In one process embodiment, this invention relates to a process for preparing a lactone of the formula

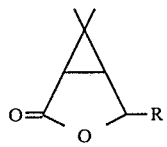

wherein R is hydrogen or a $CX_3$ group, and each X is a chlorine or bromine atom, which comprises cyclizing an optically inactive diazo ester of the formula

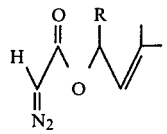

by intramolecular carbenoid cyclization.

In other process aspects, this invention relates to processes for the production of novel intermediates, for example, malonic and alkanoylacetic esters of 3-methyl-2-buten-2-ol or a 1,1,1-trihalo-4-methyl-3-penten-2-ol, as well as diazo derivatives of the esters, and 1-alkoxycarbonyl-substituted lactones, all useful as starting materials for the production of lactones represented by the aforesaid formula.

In yet another process aspect, this invention relates to a process for preparing, essentially free of the trans isomer, a cis-3-(2,2-dihalovinyl)-2,2-dimethylcyclopropanecarboxylic acid of the formula

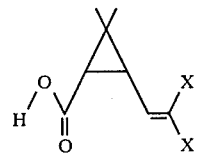

wherein the X's are the same or different, each X is a chlorine or bromine atom, and the carboxy and dihalovinyl groups are cis with respect to each other, which comprises subjecting to the Boord reaction, for example, treating with zinc and acetic acid, a compound of the formula

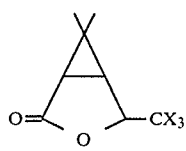

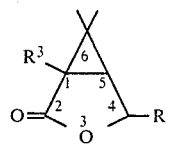

wherein the X's are the same or different and have the values given above, thereby simultaneously opening the lactone ring and eliminating one X atom.

In composition aspects, this invention relates to novel intermediates useful for the production of cis-3-(2,2-dihalovinyl)-2,2-dimethylcyclopropanecarboxylic acids and lower alkyl esters, from which pyrethroid insecticides may be prepared as described above.

The composition embodiments of the invention can be represented collectively by structural formulae I, II and III below, wherein R is a hydrogen atom or a $CX_3$ group, the X's are the same or different, each X is a chlorine or bromine atom, $R^1$ is lower alkyl or lower alkoxy, $R^2$ is hydrogen, lower alkoxycarbonyl, or lower alkanoyl, and $R^3$ is hydrogen or lower alkoxycarbonyl. The term "lower" as used herein to modify expressions such as alkyl, alkoxy, etc., means a chain of 1–6, preferably 1–4 carbon atoms.

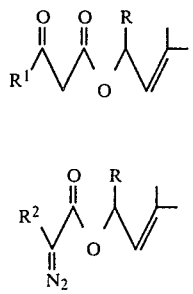

The composition embodiments of formula I are esters of alkanoylacetic and malonic acids, i.e., $R^1$ is lower alkyl or lower alkoxy, respectively. These novel esters may be prepared by esterifying 3-methyl-2-buten-1-ol or 1,1,1-trihalo-4-methyl-3-penten-2-ols; for example, with diketene or a lower alkylmalonyl chloride [see, e.g., U.S. Pat. No. 2,167,168, Kaneda, et al., *Bull. Chem. Soc. Japan*, 40, 228 (1967), and Blomquist, *J. Am. Chem. Soc.*, 70, 36 (1948)].

The composition embodiments of formula II, viz., the diazo derivatives of the aforesaid esters, and the lactones of formula III, can be produced from the esters of formula I by process embodiments of this invention, as can the cis-3-(2,2-dihalovinyl)-2,2-dimethylcyclopropane carboxylic acids and lower alkyl esters—all as described hereinafter.

In preferred embodiments of this invention, the $R^2$ group is cleaved from the diazo derivatives of formula II, and the $R^3$ group is cleaved from the lactones of formula III when $R^2$ is lower alkanoyl and $R^3$ is lower alkoxycarbonyl, respectively, values arising when $R^1$ is lower alkyl and lower alkoxy, respectively, in the ester precursors of formula I. It will be apparent, therefore, that the exact nature of the $R^1$ group is not critical. Therefore, contemplated equivalents of the compounds of formula I, and corresponding compounds of formulae II and III prepared from compounds of formula I by processes of this invention, are those compounds wherein $R^1$ is, e.g., alkyl or alkoxy of more than 6 carbon atoms, e.g, octyl and octyloxy; aryl and aryloxy, e.g., phenyl and phenoxy; aralkyl and aralkoxy, e.g., benzyl and benzyloxy, each of the foregoing bearing one or more simple substituents, e.g., halo, nitro, alkyl and alkoxy.

Processes and composition embodiments of this invention are exemplified in the following diagram. The invention is not to be construed as limited to the specific embodiments which are illustrated.

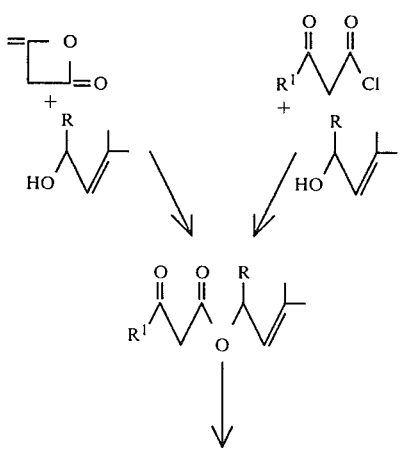

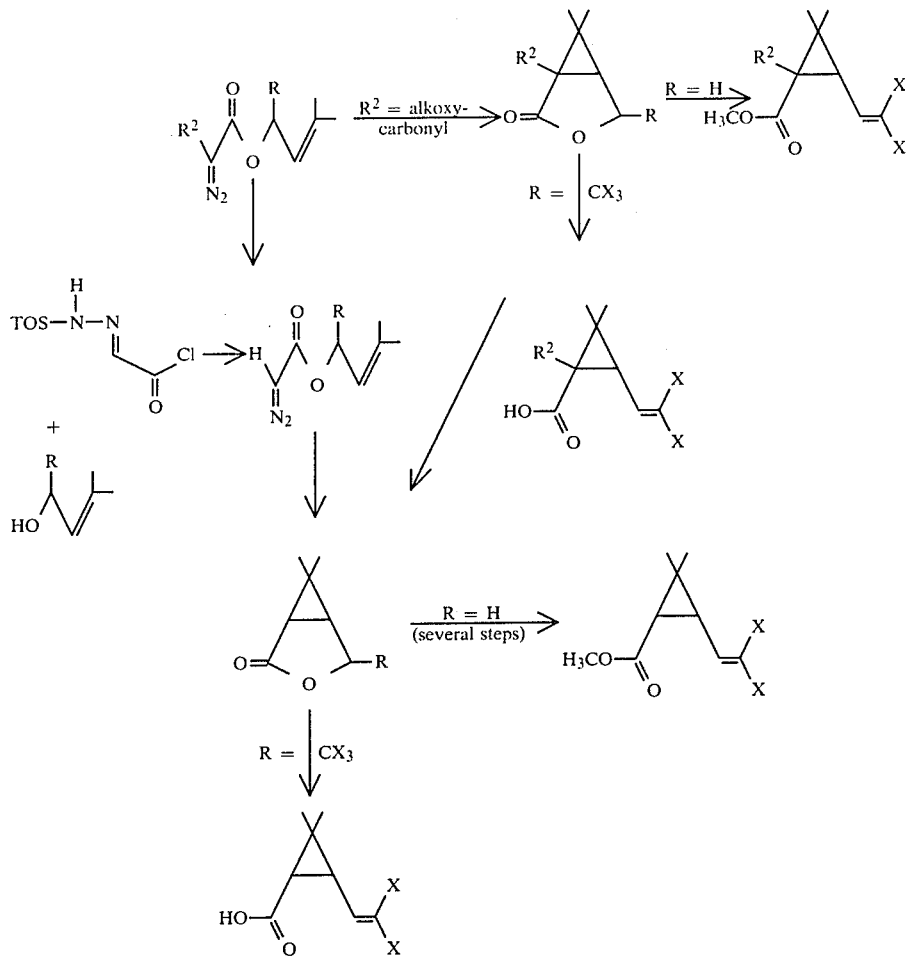

In one process embodiment, an ester of formula I is subjected to a diazo transfer reaction, as described, for example, in Regitz, *Synthesis*, 351 (1972), by reacting it with an azide, such as an arenesulfonyl azide, e.g., tosyl azide, or "polymer-bound" sulfonyl azide [see W. R. Roush, et al., *Tetrahedron Letters*, 1391 (1974)], to produce the corresponding diazo compound of formula II.

When the ester of formula I is a 3-methyl-2-butenyl alkanoylacetate or a 3-methyl-1-trihalomethyl-2-butenyl alkanoylacetate ($R^1$ is lower alkyl), a 3-methyl-2-butenyl or 3-methyl-1-trihalomethyl-2-butenyl 2-diazoalkanoylacetate (formula II, $R^2$ is lower alkanoyl), respectively, is produced. Preferably, without isolation of this intermediate, the alkanoyl group is cleaved therefrom, e.g., with base, preferably aqueous sodium hydroxide, as described in Regitz, loc. cit., to yield directly a 3-methyl-2-butenyl or 3-methyl-1-trihalomethyl-2-butenyl diazoacetate (formula II, $R^2$ is hydrogen), respectively. 3-Methyl-2-butenyl or a 3-methyl-1-trihalomethyl-2-butenyl acetoacetate are especially preferred as the ester of formula I, since they may be prepared readily from diketene.

When the ester of formula I is a 3-methyl-2-butenyl or 3-methyl-1-trihalomethyl-2-butenyl malonate ($R^1$ is lower alkoxy), it is preferred that the ethyl ester be employed in the diazo transfer reaction, producing an ethyl 3-methyl-2-butenyl or 3-methyl-1-trihalomethyl-2-butenyl diazomalonate (formula II, $R^2$ is ethoxycarbonyl).

It is preferable, however, to prepare a diazoacetate, rather than a diazomalonate, since the diazoacetate contains the hydrogen atom ultimately desired at C-1 of the cis-3-(2,2-dihalovinyl)-2,2-dimethylcyclopropanecarboxylic acid or ester. Thus, it is preferred to use a 3-methyl-2-butenyl or 3-methyl-1-trihalomethyl-2-butenyl alkanoylacetate (formula I, $R^1$ is lower alkyl, e.g. methyl) as the starting material, and an acetoacetate is especially preferred.

A second process embodiment, also within the scope of this invention, for producing the preferred 3-methyl-2-butenyl or 3-methyl-1-trihalomethyl-2-butenyl diazoacetate is to esterify 3-methyl-2-buten-1-ol or a 1,1,1-trihalo-4-methyl-3-penten-2-ol with a hydrazone, e.g., the tosyl hydrazone, of glyoxoyl chloride.

In a third process embodiment, an optically inactive diazo derivative of formula II (compounds of formula II are chiral when R is $CX_3$), wherein $R^2$ is hydrogen or lower alkoxycarbonyl, which may be prepared as described above, is cyclized, e.g., by intramolecular carbenoid cyclization, as disclosed, for example, in House, et al., *J. Org. Chem.*, 33, 53 (1968), by treatment with a copper-containing catalyst, thereby yielding a bicyclic lactone, viz., a 6,6-dimethyl-2-oxo-3-oxabicyclo[3.1.0-]hexane or a 4-trihalomethyl-6,6-dimethyl-2-oxo-3-oxabicyclo[3.1.0]hexane of formula III, when R is H or $CX_3$, respectively. If the copper-containing catalyst is not optically active, a racemic lactone is obtained, but the cyclization affords an optically active lactone when chiral copper-containing catalysts, described below, are used. An unexpected result of using an achiral or racemic catalyst is that, whereas there are two possible racemic pairs of the 4-trihalomethyl-substituted lactone (4 optical isomers), only one racemic pair is produced, the (1R,4R,5S) optical isomer and its mirror image. Preferably, the starting compound is a diazoacetate, thereby producing a compound of formula III wherein $R^3$ is hydrogen.

Racemic mixtures or optically active enriched mixtures of the lactones described herein are resolved by methods known in the art, yielding the individual optically active isomers; for example, Nozaki, et al., *Tetrahedron*, 24, 3655 (1968) suggests opening the lactone ring, resolution of the acid, followed by lactonization.

It will be evident to those skilled in the art that other compounds capable of generating the carbenoid intermediates so derived from the aforesaid diazo derivatives of formula II can also be employed to produce bicyclic lactones of formula III.

Copper-containing catalysts which may be employed to produce racemic lactones include achiral or racemic coordination complexes of copper, e.g., cupric acetylacetonate, cupric salicylaldehydeiminate, cupric ethylacetoacetate, as well as cuprous oxide, cupric oxide, cuprous chloride, cupric acetate, and metallic copper. Of these, achiral or racemic coordination complexes are preferred, and cupric acetylacetonate is especially preferred.

To effect cyclization to an optically active lactone, chiral binuclear copper-containing catalysts selected from [N-(2-hydroxyethylate)salicylideneaminato]copper(II) binuclear complexes are employed. Examples of these catalysts include optically active bis[2-butoxy-α-(2-butoxy-5-methylphenyl)-α-[1-[[(2-hydroxyphenyl)methylene]amino]ethyl]-5-methylbenzenemethanolato(2-)]-copper and bis[2-butoxy-α-[2-butoxy-5-(1,1-dimethylethyl)phenyl]-5-(1,1-dimethylethyl)-α-[1-[[2-hydroxyphenyl)methylene]amino]ethyl]benzenemethanolato(2-)]-copper. Catalysts of (S) stereochemistry, e.g., bis[2-butoxy-5-methylphenyl)-α-[(S)-1-[[(2-hydroxyphenyl)methylene]amino]ethyl]-5-methylbenzenemethanolato(2-)]-copper and bis[2-butoxy-α-[2-butoxy-5-(1,1-dimethylethyl)phenyl]-5-(1,1-dimethylethyl)-α-[(S)-1-[[2-hydroxyphenyl)methylene]amino]ethyl]benzenemethanolato(2-)]-copper, are preferred because they afford optically active lactones which may be carried, by processes described below, to cis-3-(2,2-dihalovinyl)2,2-dimethylcyclopropanecarboxylic acids or esters, which are optically active due to enrichment with the (1R,3R) isomers. Among these catalysts, bis[2-butoxy-α-[2-butoxy-5-(1,1-dimethylethyl)phenyl]-5-(1,1-dimethylethyl)-α-[(S)-1-[[2-hydroxyphenyl)methylene]amino]ethyl]benzenemethanolato(2-)]-copper is especially preferred. Catalysts of (R) stereochemistry give rise ultimately to acids or esters which are rich in the (1S,3S) enantiomers. The catalysts may be prepared from optically active ethyl alanine by coupling with a Grignard reagent, producing a salicylaldimine from the resultant amino alcohol, and treating the imine with cupric acetate, all according to the method disclosed by Aratini, et al. in *Tetrahedron Letters*, 1707 (1975), which disclosure is incorporated herein by reference.

Aprotic solvents may be employed in the cyclization, e.g., aromatic hydrocarbons and ethers, preferably toluene, benzene, n-octane, cyclohexane, or dioxane. In general, dioxane is preferred, but toluene is preferred for the tribromomethyl compounds. Improved yields are obtained if the reaction is conducted at high dilution.

In a fourth process embodiment, a bicyclic lactone of formula III, wherein $R^3$ is a lower alkoxycarbonyl group, preferably methoxycarbonyl, is subjected to dealkoxycarbonylation, e.g., by treatment with lithium chloride in a polar solvent selected from hexamethylphosphoric triamide, dimethylformamide and dimethylsulfoxide, or mixtures thereof with water, cleaving the lower alkoxycarbonyl group and producing the corresponding lactone of formula III wherein $R^3$ is hydrogen. A starting lactone produced as described above using a chiral catalyst of (S) stereochemistry affords a cleaved optically active lactone which can be carried, as described below, to cis-3-(2,2-dihalovinyl)-2,2-dimethylcyclopropanecarboxylic acids or esters, which are optically active due to enrichment with the (1R,3R) isomers.

In a fifth process embodiment, a bicyclic lactone of formula III, wherein R is hydrogen, is converted into a lower alkyl cis-3-(2,2-dihalovinyl)-2,2-dimethylcyclopropanecarboxylate. For example, Sevrin, et al., *Tetr. Letters*, 3915 (1976) describe the treatment of 6,6-dimethyl-2-oxo-3-oxabicyclo[3.1.0]hexane with base to open the ring, followed by acidification and methylation with diazomethane, producing methyl cis-3-hydroxymethyl-2,2-dimethylcyclopropanecarboxylate. The alcohol is then oxidized to methyl cis-3-formyl-2,2-dimethylcyclopropanecarboxylate. Japan. Kokai 76/122041 discloses the addition of a tri- or tetrahalomethane to the methyl 3-formyl-2,2-dimethylcyclopropanecarboxylate, followed by acylation of the resulting 3-(1-hydroxy-1-trihalomethyl)derivative and reduction of the acylated compound with metallic zinc to afford a methyl 3-(2,2-dihalovinyl)-2,2-dimethylcyclopropanecarboxylate. It is preferred to employ the lactone wherein $R^3$ is hydrogen, since 6,6-dimethyl-2-oxo-3-oxabicyclo[3.1.0]hexane yields directly a lower alkyl cis ester which may be converted into a pyrethroid insecticide by methods well known in the art and referred to above, i.e., U.S. Pat. No. 4,034,163. In the case that $R^3$ is lower alkoxycarbonyl, the resultant 1-alkoxycarbonylcyclopropanecarboxylate may be dealkoxycarbonylated, e.g., as disclosed in U.S. Pat. No. 4,000,180, and then converted into a pyrethroid insecticide. Further, if an optically active lactone is employed, it is not only preferred that it be 6,6-dimethyl-2-oxo-3-oxabicyclo[3.1.0]hexane, but that the optical activity be due to enrichment with the (1R,5S) isomer, since an optically active cyclopropanecarboxylic enriched with the (1R,3R) isomer is then obtained. Optically active 6,6-dimethyl-2-oxo-3-oxabicyclo[3.1.0]hexane which is rich in the (1R,5S) isomer is obtained, e.g., by the process embodiments described above, provided that the diazo ester is cyclized with a chiral binuclear copper-containing catalyst having (S) stereochemistry.

In a sixth process embodiment, a bicyclic lactone of the formula III, wherein R is $CX_3$, is subjected to the elimination reaction known as the Boord reaction, described, e.g., in J. March, "Advanced Organic Chemistry: Reactions, Mechanisms, and Structure," McGraw-Hill Book Co., Inc., New York, N.Y., 1968, p. 771, by treatment with a metal selected from zinc, magnesium, sodium, or coordination complexes of Cr(II), in a solvent selected from acetic acid, alcohols such as ethanol, and ethers, such as tetrahydrofuran and diethyl ether, and mixtures thereof, thereby simultaneously opening the lactone ring, eliminating one halogen atom, and producing essentially free of the trans isomer, a cis-3-(2,2-dihalovinyl)-2,2-dimethylcyclopropanecarboxylic acid, i.e., wherein the carboxy and dihalovinyl groups are cis with respect to each other. Preferably, the metal is zinc and the solvent is a mixture of an ether and acetic acid. It is preferred that $R^3$ by hydrogen, since the cyclopropanecarboxylic acid may then be converted directly into a pyrethroid insecticide as described above, e.g., see U.S. Pat. No. 4,034,163. In the case that $R^3$ is lower alkoxycarbonyl, the resultant 1-alkoxycarbonyl-cyclopanecarboxylic acid may be dealkoxycarbonylated, e.g., via the esters as disclosed in U.S. Pat. No. 4,000,180, and then converted into a pyrethroid insecticide. Further, if an optically active lactone is employed, it is not only preferred that it be a 4-trihalomethyl-6,6-dimethyl-2-oxo-3-oxabicyclo[3.1.0]hexane, but that the optical activity be due to enrichment with the (1R,4R,5S) isomer, since an optically active cyclopropanecarboxylic acid enriched with the (1R,3R) isomer is then obtained. An optically active 4-trihalomethyl-6,6-dimethyl-2-oxo-3-oxabicyclo[3.1.0]hexane which is rich in the (1R,4R,5S) isomer is obtained, e.g., by the process embodiments described above, provided that the diazo ester is cyclized with a chiral binuclear copper-containing catalyst having (S) stereochemistry.

Since the Boord reaction involves the elimination of only one halogen atom from the trihalomethyl group at C-4 of a 4-trihalomethyl-substituted lactone of formula III, and since the trihalomethyl group is not a reactive center in the processes leading to the lactone, it will be apparent that two of the halogen atoms in the compounds of formulae I, II, or III can be replaced by other substituents in any of the processes of this invention, e.g., two of the halogen atoms can be independently hydrogen; halogen; cyano; lower alkyl of 1 to 4 carbon atoms, which may be substituted with one or more halogen atoms; and

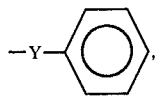

where Y is $-CH_2-$, $-O-$, $-S-$, or absent, and the phenyl group may be substituted with one or more halogen, lower alkyl (1 to 4 carbon atoms), lower haloalkyl, lower alkoxy, or lower alkylthio groups. In addition, it will be evident to those skilled in the art that various derivatives of a cis-3-(2,2-dihalovinyl)-2,2-dimethylcyclopropanecarboxylic acid, rather than the acid itself, can be obtained from the Boord reaction by varying the manner in which the lactone of formula III is opened; e.g., when the lactone is treated with methanolic potassium carbonate followed by zinc and acetic acid, a methyl dihalovinylcyclopropanecarboxylate is obtained.

In a preferred multistep process embodiment, a cis-3-(2,2-dihalovinyl)-2,2-dimethylcyclopropanecarboxylic acid is produced by treating a (±)-3-methyl-1-trihalomethyl-2-butenyl acetoacetate of formula I with tosyl azide to effect diazo transfer, followed by sodium hydroxide to cleave the acetyl group and produce a (±)-3-methyl-1-trihalomethyl-2-butenyl diazoacetate of formula II, which in turn is subjected to intramolecular carbenoid cyclization with cupric acetylacetonate to produce a 4-trihalomethyl-6,6-dimethyl-2-oxo-3-oxabicyclo[3.1.0]hexane of formula III, which is then treated in the Boord reaction with zinc and acetic acid to produce a cis-3-(2,2-dihalovinyl)-2,2-dimethylcyclopropanecarboxylic acid.

Although any compound of formulae I, II, and III wherein R is a $CX_3$ group may contain both chlorine and bromine and may be employed in the aforesaid processes, the trichloro and tribromo compounds are preferred, and the yields are generally higher with the chlorine-containing compounds. Thus, the processes disclosed above are especially well suited to preparing a cis-3-(2,2-dichlorovinyl)-2,2-dimethylcyclopropanecarboxylic acid or lower alkyl ester. The dibromovinyl acids or esters may be prepared in excellent yield by exchanging the halogen in the dichlorovinyl acid or a lower alkyl ester thereof as disclosed in the application of Kondo and Matsui, entitled "Process for Converting 2,2-Dichlorovinylcyclopropanes to Dibromovinyl Analogs," filed concurrently with application Ser. No. 875,649, parent to the instant application.

The invention will be understood more completely by reference to the following preparative examples.

In the Examples which follow, temperatures are in degrees Celsius and pressures are in mm Hg. Tetramethylsilane was employed as an internal standard for the nmr spectra. In reporting the nmr data the abbreviations have the following significance: s, singlet; d, doublet; t, triplet; q, quartet; m, multiplet. Any of the abbreviations may be proceded by b for broad or d for double, for example, d.d., double doublet; b.t., broad triplet.

EXAMPLE I

Synthesis of 4-Trihalomethyl-6,6-dimethyl-2-oxo-3-oxabicyclo[3.1.0]hexanes

A. From 3-methyl-1-trihalomethyl-2-butenyl diazoacetates

1. Preparation of 1,1,1-trichloro-4-methyl-3-penten-2-ol

To a solution of isobutene (89 g, 1.6 moles) and chloral (80 g, 0.52 mole) in about 100 ml of petroleum ether (bp, 30°–70°), maintained at −5° to −10°, was added portionwise over a period of 30–60 minutes 6.08 g of anhydrous aluminum trichloride. The solution was stirred vigorously during the addition and thereafter for five hours at −5° to −10°, then overnight at room temperature.

After diluting the solution with ether, it was washed with 50–100 ml of water, dried over magnesium sulfate and distilled. After distillation of the petroleum ether, 1,1,1-trichloro-4-methyl-4-penten-2-ol (74.9 g, 71% yield) was obtained; bp, 106°–118°/25 mm.

1,1,1-Trichloro-4-methyl-4-penten-2-ol (74 g, 0.36 mole) was heated at 140°–150° for 18 hours. After cooling, the alcohol was diluted with ether, and the ethereal solution was treated with activated charcoal. The ether was removed by evaporation to afford crystalline 1,1,1-trichloro-4-methyl-3-penten-2-ol (43.4 g, 59% yield) after recrystallization from petroleum ether.

1,1,1-Tribromo-4-methyl-3-penten-2-ol is similarly prepared by substituting bromal for chloral in the reaction.

2. Preparation of 3-methyl-1-trichloromethyl-2-butenyl acetoacetate

A mixture of 1,1,1-trichloro-4-methyl-3-penten-2-ol (20.4 g, 0.1 mole) and anhydrous sodium acetate (0.04 g) were heated together at 90°–95° until the trichloro alcohol melted. Diketene (13.2 ml, 0.11 mole) was added dropwise in one hour to the mixture maintained at 80°–83°. The mixture was then maintained at 80°–83° for an additional two hours.

The reaction mixture was diluted with ether, and the ethereal solution was washed successively with aqueous 1N hydrochloric acid, saturated aqueous sodium bicarbonate, and saturated aqueous sodium chloride. The solution was then dried over magnesium sulfate, and the ether was evaporated, leaving a residue which was distilled under vacuum, affording 3-methyl-1-trichloromethyl-2-butenyl acetoacetate (25.3 g, 88% yield); bp, 95°–96°/0.23 mm.

3. Preparation of 3-methyl-1-tribromomethyl-2-butenyl acetoacetate 1,1,1-Tribromo-4-methyl-3-penten-2-ol (6.72 g, 0.02 mole) and anhydrous sodium acetate (0.008 g) were melted together at 90°. The temperature of the mixture was then reduced to 80°, and diketene (about 2.6 ml, 0.022 mole) was added dropwise over a 10 minute period. The resulting mixture was heated at 80° for three additional hours. After cooling, the mixture was diluted with ether, and the ethereal solution was washed with 1N aqueous hydrochloric acid and then ten times with saturated aqueous sodium bicarbonate. The washed mixture was treated with activated charcoal and dried over magnesium sulfate. Evaporation of the ether afforded 3-methyl-1-tribromomethyl-2-butenyl acetoacetate (8.34 g, 99% yield) as an oily residue.

Analysis: nmr $\delta$ ppm: 6.02(d, 1H); 5.25(m, 1H); 3.53(s, 2H); 2.32(s, 3H); 1.85(m, 6H).

4. Preparation of 3-methyl-1-trichloromethyl-2-butenyl diazoacetate from 3-methyl-1-trichloromethyl-2-butenyl acetoacetate To a solution of 3-methyl-1-trichloromethyl-2-butenyl acetoacetate (5.75 g, 0.02 mole) and triethylamine (2.02 g, 0.02 mole) in 50 ml of acetonitrile was added a solution of tosyl azide (3.94 g, 0.02 mole, prepared according to the method of *Organic Synthesis Collective Volume V*, page 179A) in acetonitrile dropwise over a period of 10 minutes. The resultant mixture, containing the thus produced 3-methyl-1-trichloromethyl-2-butenyl-2-diazoacetoacetate, was stirred at room temperature for two hours and then poured into 60 ml (0.06 mole) of 1N aqueous sodium hydroxide. The resulting mixture was stirred at room temperature for 30 minutes and then extracted with about 100 ml of ether. After phase separation, the aqueous layer was extracted with an additional 150 ml portion of ether, and the ether extracts were combined. The ethereal solution was then washed ten times with 50 ml portions of 3% aqueous potassium hydroxide containing sodium chloride and then three times with 50 ml portions of saturated aqueous sodium chloride. The washed ethereal solution was dried over magnesium sulfate, and the ether was removed by evaporation, affording a brown oily residue. The residue was purified by column chromatography on silica gel using benzene as the eluent, to give 3-methyl-1-trichloromethyl-2-butenyl diazoacetate (4.63 g, 85% yield).

5. Preparation of 3-methyl-1-tribromomethyl-2-butenyl diazoacetate

To a solution of 3-methyl-1-tribromomethyl-2-butenyl acetoacetate (8.32 g, 0.0198 mole) and tosyl azide (3.9 g, 0.0198 mole) in 40 ml of acetonitrile was added dropwise over a period of 35 minutes a solution of triethylamine (2.0 g, 0.020 mole) in 10 ml of acetonitrile. The resulting mixture was stirred at room temperature for 2½ hours to give 3-methyl-1-tribromomethyl-2-butenyl diazoacetoacetate. Then 60 ml of 1N aqueous sodium hydroxide was added thereto, and the mixture was stirred at room temperature for 45 minutes. The reaction mixture was then diluted with ether, the organic phase was separated, the aqueous phase was extracted with ether, and the organic phases were combined. The ethereal solution was washed with three successive portions of 3% aqueous potassium hydroxide containing sodium chloride, then three times with saturated aqueous sodium chloride. The washed ethereal solution was dried over magnesium sulfate and treated with active charcoal. Evaporation of the ether afforded an oily residue. 3-Methyl-1-tribromomethyl-2-butenyl diazoacetate (5.78 g, 71% yield) was isolated therefrom by column chromatography.

Analysis: nmr $\delta$ ppm (CDCl$_3$): 1.85(dd, 6H); 4.82(s, 1H); 5.33(dq, 1H); 6.03(d, 1H).

6. Preparation of 3-methyl-1-trichloromethyl-2-butenyl diazoacetate from the tosyl hydrazone of glyoxyloyl chloride To a cold (0°) solution of the tosyl hydrazone of glyoxyloyl chloride (2.61 g, 0.01 mole, prepared according to the method of *Organic Synthesis Collective Volume V*, page 259), and 1,1,1-trichloro-4-methyl-3-penten-2-ol (2.035 g, 0.01 mole) in 25 ml of methylene chloride was added dropwise over a period of 20 minutes a solution of triethylamine (2.02 g, 0.02 mole) in 8 ml of methylene chloride. After stirring for one hour at 0°, the methylene chloride was evaporated at 25° under vacuum, leaving a residue. The residue was dissolved in 50 ml of benzene, and the dark brown solution was treated with activated charcoal and evaporated to give a yellow-brown oil. The oil was dissolved in methylene chloride, and the solution was washed successively twice with cold water, twice with cold aqueous sodium bicarbonate, and twice with cold water. The solution in methylene chloride was dried over sodium sulfate and evaporated at 25° under vacuum to give methyl-1-trichloromethyl-2-butenyl diazoacetate (2.67 g, 99% yield of crude product) as a viscous oil.

Analysis: ir (cm$^{-1}$): 2970, 2950, 2900, 2130, 1770, 1740, 1700, 1440, 1340, 1310, 1270, 1200, 1170, 1095, 1070, 970, 840, 830, 800, 770, 750, 630, 560, 540, 450.

3-Methyl-1-trichloromethyl-2-butenyl diazoacetate, prepared similarly, except that the triethylamine was added in two portions an hour apart, the resulting mixture was then stirred for 2.5 hours at 0°, and the product was purified by column chromatography, displayed the following nmr spectrum.

nmr $\delta$ ppm (CCl$_4$): 5.93(d, 1H); 5.23(dq,1H); 4.72(s, 1H); 1.87(t, 6H).

7. Preparation of (±)-4-trichloromethyl-6,6-dimethyl-2-oxo-3-oxabicyclo[3.1.0]hexane To a refluxing solution of cupric acetylacetonate (0.07 g, 0.27 mole) in 70 ml of dioxane was added dropdropwise over a 3½ hour period, under an argon atmosphere, a solution of (±)-3-methyl-1-trichloromethyl-2-butenyl diazoacetate (1.09 g, 0.004 moles) and cupric acetylacetonate (0.007 g, 0.027 mmole) in 10 ml of dioxane. The reaction mixture was then heated under reflux for one hour and evaporated to dryness, yielding a residue which was dissolved in ether. The ethereal solution was washed successively with two portions of aqueous 1N hydrochloric acid, two portions of aqueous sodium bicarbonate, and twice with saturated aqueous sodium chloride. After drying the solution over magnesium sulfate, the ether was evaporated to afford a pale yellow oil, which was purified by column chromatograpy on a silica gel column using a 9/1 mixture of n-hexane/ethyl acetate as the eluent, to give (±)-4-trichloromethyl-6,6-dimethyl-2-oxo-3-oxabicyclo[3.1.0-]hexane (0.55 g, 53% yield).

8. Preparation of optically active 4-trichloromethyl-6,6-dimethyl-2-oxo-3-oxabicyclo[3.1.0]hexane A solution of (±)-3-methyl-1-trichloromethyl-2-butenyl diazoacetate (0.544 g, 2 mmole) in dioxane (5 ml) was added dropwise over a period of about 4.5 hours to a suspension of bis-[2-butoxy-α-[2-butoxy-5-(1,1-dimethylethyl)phenyl]-5-(1,1-dimethylethyl)-α-[(S)-1-[[(2-hydroxyphenyl)methylene]amino]ethyl]benzenemethanolato-(2-)] copper (0.762 g, 0.05 mmole) in dioxane (35 ml) at 100°–105°. When the evolution of nitrogen began, the temperature was slowly lowered to 50° and maintained at 50° throughout the addition. After the addition of the 3-methyl-1-trichloromethyl-2-butenyl diazoacetate was completed, the reaction mixture was stirred at 50° for 2 hours. The reaction mixture was then evaporated to dryness under vacuum and the residue dissolved in diethyl ether. The ethereal solution was washed with a 1N aqueous solution of hydrochloric acid until the washings did not turn blue when tested with aqueous ammonia, then washed once with a saturated aqueous solution of sodium chloride and dried over magnesium sulfate. The ether was evaporated under vacuum, and the crude 4-trichloromethyl-6,6-dimethyl-2-oxo-3-oxabicyclo[3.1.0]hexane enriched with the (1R,4R,5S) isomer (0.47 g) was converted by zinc reduction to 3-(2,2-dichlorovinyl)-2,2-dimethylcyclopropanecarboxylic acid. The acid, after purification by column chromotagraphy, had an optical rotation of $[\alpha]_D^{18.5} = +4.7°$ (CHCl$_3$). The optical yield of (1R,3R)-3-(2,2-dichlorovinyl)-2,2-dimethylcyclopropanecarboxylic acid from the (±)-3-methyl-1-trichloromethyl-2-butenyl diazoacetate was calculated to be about 14%.

Optically active 4-tribromomethyl-6,6-dimethyl-2-oxo-3-oxabicyclo[3.1.0]hexane enriched with the (1R,4R,5S) isomer is similarly prepared from (±)-3-methyl-1-tribromomethyl-2-butenyl diazoacetate.

Optically active lactones enriched with the (1S,4S,5R) isomers are prepared by substituting the (R) catalyst for the (S) catalyst specified above.

9. Preparation of (±)-4-tribromomethyl-6,6-dimethyl-2-oxo-3-oxabicyclo[3.1.0]hexane To a refluxing solution of cupric acetylacetonate (0.005 g, 0.019 mmole) in 40 ml of toluene was added dropwise over a period of 2.5 hours under an atmosphere of argon gas a solution of (±)-3-methyl-1-tribromomethyl-2-butenyl diazoacetate (0.203 g, 0.005 ml) in 10 ml of toluene. The mixture was then heated under reflux for one hour. After cooling, the reaction mixture was washed successively with two portions of 1N aqueous hydrochloric acid, once with saturated aqueous sodium bicarbonate, and twice with saturated aqueous sodium chloride. After drying over magnesium sulfate, the solution was evaporated to give a yellow oil as the residue. The residue was purified by column chromatography on a silica gel column using 9/1 n-hexane/ethyl acetate as the eluent, yielding (±)-4-tribromomethyl-6,6-dimethyl-2-oxo-3-oxabicyclo[3.1.0-]hexane (0.053 g, yield 28%); mp 101°–103° after recrystallization from n-hexane.

Analysis: Calculated for $C_8H_9Br_3O_2$: C,25.50; H,2.41; Found: C,25.52; H,2.36.

nmr δ ppm (CDCl$_3$): 1.28(2s, 6H); 2.18 (d, 1H). 2.37(d, 1H); 4.58 (s, 1H).

The nmr spectrum indicates that the lactone is the (1S,4S,5R)/(1R,4R,5S) racemic mixture.

10. Preparation of 1-trichloromethyl-3-methyl-2-butenyl-2-diazoacetoacetate

To a solution of 1-trichloromethyl-3-methyl-2-butenyl acetoacetate (0.575 g, 2 mmole) and triethylamine (0.404 g, 4 mmole) in 10 ml of acetonitrile was added 1 g of polymer-bound sulfonyl azide (prepared by the method of Roush, et al., loc. cit.). The mixture was stirred overnight at room temperature and filtered. The filter cake was washed with ether, and the slurry was filtered. Solvent was removed by evaporation from the combined filtrates to give 1-trichloromethyl-3-methyl-2-butenyl 2-diazoacetoacetate (0.60 g, 96% yield).

Analysis: nmr δ ppm: 6.03 (d, 1H); 5.28 (bd, 1H); 2.45 (s, 3H); 1.90 (d, 6H).

B. From lower alkyl 3-methyl-1-trichloromethyl-2-butenyl diazomalonates

1. Preparation of ethyl 3-methyl-1-trichloromethyl-2-butenyl malonate

To a solution of 1,1,1-trichloro-4-methyl-3-penten-2-ol (7.98 g, 0.0392 mole) and pyridine (3.10 g, 0.0392 mole) in 8 ml of ether was added dropwise a solution of ethyl malonyl chloride (5.87 g, 0.039 mole) in 4 ml of ether. The reaction mixture was then stirred overnight at room temperature.

The reaction mixture was diluted with ether and then washed with aqueous 1N hydrochloric acid, then aqueous sodium bicarbonate, followed by aqueous medium chloride. The washed mixture was dried over magnesium sulfate, the ether was removed by evaporation, and the residue was distilled to afford ethyl 3-methyl-1-trichloromethyl-2-butenyl malonate (5.68 g, 46% yield); bp, 104°–105°/0.3 mm.

Analysis: nmr δ ppm: 6.00(d, 1H); 5.32(dq, 1H); 4.18(dd, 2H); 3.35(s, 2H); 1.88(m, 6H); 1.30(t, 3H).

2. Preparation of ethyl 3-methyl-1-trichloromethyl-2-butenyl diazomalonate

To a solution of ethyl 3-methyl-1-trichloro-methyl-2-butenyl malonate (5.63 g, 0.0177 mole) and triethylamine (1.79 g, 0.0177 mole) in 40 ml of acetonitrile was added dropwise a solution of tosyl azide (3.487 g, 0.0177 mole) in 10 ml of acetonitrile. After the addition, the mixture was stirred overnight at room temperature.

The acetonitrile was then evaporated from the solution at room temperature under vacuum, yielding a residue, which was dissolved in ether. The ethereal solution was washed successively with three portions of 3% aqueous potassium hydroxide and once with aqueous sodium chloride. After drying the solution over magnesium sulfate, the ether was evaporated to yield ethyl 3-methyl-1-trichloromethyl-2-butenyl diazomalonate (5.91 g, 85% yield) as the residue.

Analysis: nmr δ ppm (CCl₄): 6.03(d, 1H); 5.30(dq, 1H); 4.27(dd, 2H); 1.88(m, 6H); 1.33(t, 3H).

3. Preparation of ethyl (±)-4-trichloromethyl-6,6-dimethyl-2-oxo-3-oxabicyclo[3.1.0]hexane-1-carboxylate To a refluxing suspension of copper powder (5.0 g, 0.079 mole) in 240 ml of n-octane was added dropwise in one hour a solution of ethyl (±)-3-methyl-1-trichloromethyl-2-butenyl diazomalonate (5.0 g, 0.0146 mole) in 60 ml of n-octane. The reaction mixture was then heated under reflux for 2½ hours and filtered. The n-octane was removed from the filtrate by evaporation under vacuum, yielding a residue which was distilled under vacuum to give ethyl (±)-4-trichloromethyl-6,6-dimethyl-2-oxo-3-oxabicyclo-[3.1.0]hexane-1-carboxylate as a highly viscous oil (2.47 g, 54% yield); bp, 123°–125°/0.3 mm.

Analysis: nmr δ ppm (CCl₄): 4.47(s, 1H); 4.23(dd, 2H); 2.67(s, 1H); 1.32(m, 9H).

4. Preparation of methyl (±)-4-trichloromethyl-6,6-dimethyl-2-oxo-3-oxabicyclo[3.1.0]hexane-1-carboxylate To a refluxing suspension of copper powder (6.6 g, 0.104 mole) in 320 ml of n-octane was added dropwise in one hour a solution of methyl (±)-3-methyl-1-trichloromethyl-2-butenyl diazomalonate (6.6 g, 0.02 mole, prepared as described above for the ethyl ester) in 80 ml of n-octane. The reaction mixture was heated for 2½ hours under reflux and then filtered while hot. The n-octane was evaporated from the filtrate under vacuum to produce a residue which was dissolved in ethyl acetate. The solution was washed successively with aqueous 1N hydrochloric acid, aqueous sodium bicarbonate, and aqueous sodium chloride. After drying the solution over magnesium sulfate, the ethyl acetate was removed by evaporation, yielding methyl (±)-4-trichloromethyl-6,6-dimethyl-2-oxo-3-oxabicyclo[3.1.0]hexane-1-carboxylate (5.77 g, 96% yield) as an oil. Trituration of the oil with ether afforded the crystalline lactone; mp, 118°–120°.

Analysis: Calculated for C₁₀H₁₁O₄Cl₃: C, 39.83; H, 3.68; Found: C, 39.57; H, 3.56.

nmr δ ppm (CDCl₃): 4.39(s,1H); 3.76 (s,3H); 2.61(s,1H); 1.30 (s, 6H).

mass spec. m/e: 300, 109, 100, 33, 18. molecular weight (CHCl₃): 295

The nmr spectrum indicates that the lactone is the (1S, 4S,5R)/(1R,4R,5S) racemic mixture.

5. Preparation of 4-trichloromethyl-6,6-dimethyl-2-oxo-3-oxabicyclo[3.1.0]hexane To a solution of methyl 4-trichloromethyl-6,6-dimethyl-2-oxo-3-oxabicyclo[3.1.0]hexane-1-carboxylate (1.52 g, 0.005 mole) in 10 ml of hexamethylphosphoric triamide was added lithium chloride (0.42 g, 0.010 mole). After heating at 75° for two hours, the cooled reaction mixture was diluted with ether. The ethereal solution was washed with water, dried over magnesium sulfate, and the ether was removed by evaporation, yielding a residue which was purified by column chromatography on silica gel using 9/1 n-hexane/ethylacetate as the eluent to give 4-trichloromethyl-6,6-dimethyl-2-oxo-3-oxabicyclo[3.1.0]hexane (0.34 g, 28% yield) as an oil.

Analysis: nmr δ ppm (CDCl₃): 4.60(s, 1H); 2.37(d, 1H); 2.15(d, 1H); 1.28(s, 6H).

mass spec. m/e: 243, 125, 100, 97, 30.

Following the above procedure, the same compound is prepared from ethyl 4-trichloromethyl-6,6-dimethyl-2-oxo-3-oxabicyclo[3.1.0]hexane-1-carboxylate.

EXAMPLE II

Synthesis of 6,6-Dimethyl-2-oxo-3-oxabicyclo[3.1.0]hexane

1. Preparation of 3-methyl-2-butenyl acetoacetate

A mixture of 3-methyl-2-buten-1-ol (21.2 g, 0.25 mole) and anhydrous sodium acetate (0.1 g) was cooled to 0°. Diketene (36 ml, 0.3 mole) was added dropwise over a period of 1.5 to 2 hours. The reaction mixture was then heated to 75°–80°, and this temperature was maintained for one hour. The mixture was diluted with ether. The ethereal solution was washed successively with aqueous 1N hydrochloric acid, saturated aqueous sodium bicarbonate, saturated aqueous sodium chloride, and then dried over magnesium sulfate. The ether was evaporated, leaving a residue which was distilled under vacuum, affording 3-methyl-2-butenyl acetoacetate (32.1 g, 76% yield); bp 114°–117°/18–19 mm.

2. Preparation of 3-methyl-2-butenyl diazoacetate

A solution of 3-methyl-2-butenyl acetoacetate (7.4 g, 0.0435 mole) and p-toluenesulfonyl azide was prepared in acetonitrile. Triethylamine (4.40 g) in acetonitrile was added dropwise to this solution over a period of 10 minutes, and the stirred reaction mixture was maintained at room temperature for 2 hours. An aqueous 1N solution of sodium hydroxide (130 ml, 0.13 mole) was added and stirring continued for 45 minutes. Ether and aqueous sodium chloride were added to the mixture. After phase separation, the aqueous layer was washed consecutively with aqueous 1N sodium hydroxide (3 times) and a saturated aqueous solution of sodium chloride (twice). The washed ethereal solution was dried over magnesium sulfate and treated with active charcoal. The residue, after evaporation, was identified as 3-methyl-2-butenyl diazoacetate (5.72 g, 85% yield).

Analysis: nmr δ ppm: 1.8 (m, 6H); 4.6 (s, 1H); 4.8 (m, 2H); 5.4 (m, 1H).

3. Preparation of (±)-6,6-dimethyl-2-oxo-3-oxabicyclo[3.1.0]hexane

A solution of 3-methyl-2-butenyl diazoacetate (41.3 mmole, 6.36 g) in dioxane (20 ml) was added dropwise to a refluxing solution of cupric acetylacetonate (1.03 mmole, 0.27 g) in dioxane (400 ml) over a period of 7 hours under an argon atomosphere. After completion of the addition, the reaction mixture was heated under reflux for 1 hour. The crude reaction mixture was distilled to afford (±)-6,6-dimethyl-2-oxo-3-oxabicyclo[3.1.0]hexane (3.85 g, 75% yield); bp 110°, 16 mm Hg.

4. Preparation of optically active 6,6-dimethyl-2-oxo-3-oxabicyclo[3.1.0]hexane A solution of 3-methyl-2-butenyl diazoacetate (980 mg, 6.4 mmoles) in dioxane (15 ml) was added dropwise to a solution of bis[2-butoxy-α-[2-butoxy-5-(1,1-dimethylethyl)phenyl]-5-(1,1-dimethylethyl)-α-[(S)-1-[[2-hydroxyphenyl)methylene]amino]ethyl]benzenemethanolato (2-)]-copper (83 mg, 0.064 mmole) in dioxane (55 ml) at 110°. When the evolution of nitrogen started, the temperature was slowly lowered to 52°–3°. The addition took 5.5 hours, and the evolution of almost theoretical amounts of nitrogen was observed. After the addition was completed, the reaction mixture was stirred at 52°–3° for 2 hours, evaporated to dryness, and distilled under vacuum to afford 6,6-dimethyl-2-oxo-3-oxabicyclo[3.1.0]hexane enriched with the (1R,5S) isomer (500 mg). The optical rotation of the product was $[\alpha]_D^{29} = -53.5°$ (CHCl$_3$).

The product was then treated with base, acidified, then methylated as described by Sevrin, et al., *Tetrahedron Letters*, 3915 (1976), before oxidation to methyl cis-3-formyl-2,2-dimethylcyclopropanecarboxylate. The latter was then converted to a lower alkoxy 3-(2,2-dichlorovinyl)-2,2-dimethylcyclopropanecarboxylate by the procedure disclosed in Japan. Kokai 76/122041. The ester was hydrolyzed, and the optical activity of the resulting cis-3-(2,2-dichlorovinyl)-2,2-dimethylcyclopropanecarboxylic acid was $[\alpha]_D = +16.7$ (CHCl$_3$), corresponding to an optical yield of about 58% (1R,3R) isomer.

EXAMPLE III

Synthesis of cis-3-(2,2-Dihalovinyl)-2,2-dimethylcyclopropanecarboxylic Acids

A. Preparation of cis-3-(2,2-dichlorovinyl)-2,2-dimethylcyclopropanecarboxylic acid To a suspension of zinc powder (0.52 g, 0.008 mole) in 0.6 ml of acetic acid and 3 ml of ether was added dropwise over a period of 15 minutes a solution of 4-trichloromethyl-6,6-dimethyl-2-oxo-3-oxabicyclo[3.1.0]hexane (0.487 g, 0.002 mole) in 3 ml of ether. The mixture was stirred for two hours at room temperature, 30 ml of ether and 5 ml of water were added, and the mixture was then filtered through Celite filter aid. The organic layer was separated, washed twice with saturated aqueous sodium chloride, dried over magnesium sulfate, and the ether was evaporated to give crystalline cis-3-(2,2-dichlorovinyl)-2,2-dimethylcyclopropanecarboxylic acid (0.405 g, 97% yield).

Analysis: nmr δ ppm (CDCl$_3$): 1.18(s, 6H); 1.92(m, 2H); 6.15(d, 1H); 13.27(bs, 1H).

The presence in the nmr spectrum of the single doublet at 6.15 ppm indicates that only the cis isomer is present.

B. Preparation of cis-3-(2,2-dibromovinyl)-2,2-dimethylcyclopropanecarboxylic acid To a chilled suspension of zinc powder (0.494 g, 0.0076 mole) in 0.57 ml of acetic acid and 3 ml of ether was added dropwise over a period of 20 minutes a solution of 4-tribromomethyl-6,6-dimethyl-2-oxo-3-oxabicyclo[3.1.0]hexane (0.72 g, 0.0019 mole) in 5 ml of ether. The mixture was stirred at 0° for one hour. After adding 30 ml of ether and 5 ml of water, the mixture was filtered through Celite filter aid. The organic layer was separated, washed three times with saturated aqueous sodium chloride, dried magnesium sulfate, and the ether was removed by evaporation to give crystalline cis-3-(2,2-dibromovinyl)-2,2-dimethylcyclopropanecarboxylic acid (0.489 g, 86% yield); mp, 112°–114° after recrystallization from n-hexane.

Analysis: nmr δ ppm (CDCl$_3$): 1.27(s, 6H); 1.97(m, 2H); 6.67(d, 1H); 11.3(bs, 1H).

The presence in the nmr spectrum of the single doublet at 6.67 ppm shows that only the cis isomer is present.

If an optically active 4-trihalomethyl-6,6-dimethyl-2-oxo-3-oxabicyclo[3.1.0]hexane is employed, e.g., enriched with the (1R,4R,5S) optical isomer, an optically active cis-3-(2,2-dihalovinyl)-2,2-dimethylcyclopropanecarboxylic acid, e.g., enriched with the (1R,3R) isomer, is obtained.

We claim:

1. A compound of the formula

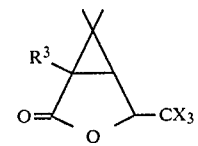

wherein each X is the same or different and is a chlorine or bromine atom, and R$_3$ is lower alkoxycarbonyl.

2. A compound of claim 1 wherein X is a chlorine atom.

3. A compound of claim 1 which is optically active due to enrichment with the 1R,4R,5S or 1S,4S,5R optical isomer.

4. A compound of claim 1 which is a racemic mixture of the 1R,4R,5S optical isomer and its mirror image.

* * * * *